(12) United States Patent
Hayn et al.

(10) Patent No.: US 12,329,871 B2
(45) Date of Patent: Jun. 17, 2025

(54) AUTOMATICALLY MOVING DISINFECTION ROBOT FOR DISINFECTING SURFACES

(71) Applicant: Vorwerk & Co. Interholding GmbH, Wuppertal (DE)

(72) Inventors: Henning Hayn, Hilden (DE); Andrej Mosebach, Unna (DE); Georg Hackert, Bochum (DE)

(73) Assignee: Vorwerk & Co. Interholding GmbH, Wuppertal (DE)

( * ) Notice: Subject to any disclaimer, the term of this patent is extended or adjusted under 35 U.S.C. 154(b) by 917 days.

(21) Appl. No.: 17/501,056

(22) Filed: Oct. 14, 2021

(65) Prior Publication Data
US 2022/0125977 A1    Apr. 28, 2022

(30) Foreign Application Priority Data
Oct. 23, 2020   (DE) ................... 10 2020 127 988.4

(51) Int. Cl.
| | | |
|---|---|---|
| *G01N 21/00* | (2006.01) | |
| *A61L 2/10* | (2006.01) | |
| *A61L 2/14* | (2006.01) | |
| *A61L 2/22* | (2006.01) | |
| *A61L 2/24* | (2006.01) | |
| *A61N 5/00* | (2006.01) | |
| *B25J 9/16* | (2006.01) | |
| *B25J 11/00* | (2006.01) | |
| *G01N 23/00* | (2006.01) | |

(52) U.S. Cl.
CPC .................. *A61L 2/24* (2013.01); *A61L 2/10* (2013.01); *A61L 2/14* (2013.01); *A61L 2/22* (2013.01); *B25J 9/1664* (2013.01); *B25J 11/0085* (2013.01); *A61L 2202/11* (2013.01); *A61L 2202/14* (2013.01); *A61L 2202/15* (2013.01); *A61L 2202/16* (2013.01)

(58) Field of Classification Search
CPC ..... A61L 2/10; A61L 2/20; A61L 2/24; A61L 9/14; A61L 2202/25
USPC ........ 422/24, 28; 250/492.1, 453.11, 454.11, 250/455.11
See application file for complete search history.

(56) References Cited

U.S. PATENT DOCUMENTS

2016/0271803 A1 * 9/2016 Stewart ................ B25J 11/0085

* cited by examiner

*Primary Examiner* — Monzer R Chorbaji
(74) *Attorney, Agent, or Firm* — Collard & Roe, P.C.

(57) ABSTRACT

An automatically moving disinfection robot for disinfecting surfaces has a device housing, a drive means for the movement of the disinfection robot within a surrounding area comprising at least one room, a navigation means for the navigation and self-localization of the disinfection, a disinfection means, and a control means for controlling the disinfection activity. The control means controls a locally limited disinfection in only one subregion of the room, or a locally limited disinfection of only one object, in a fully automated manner. The disinfection means has a shielding means for separating the locally limited subregion to be disinfected from adjacent subregions of the same room. The shielding means is a housing, which is open only on one side and which is placed around the object or against the surface to be disinfected, so that the disinfection only takes place within the housing, but not outside of the housing.

7 Claims, 3 Drawing Sheets

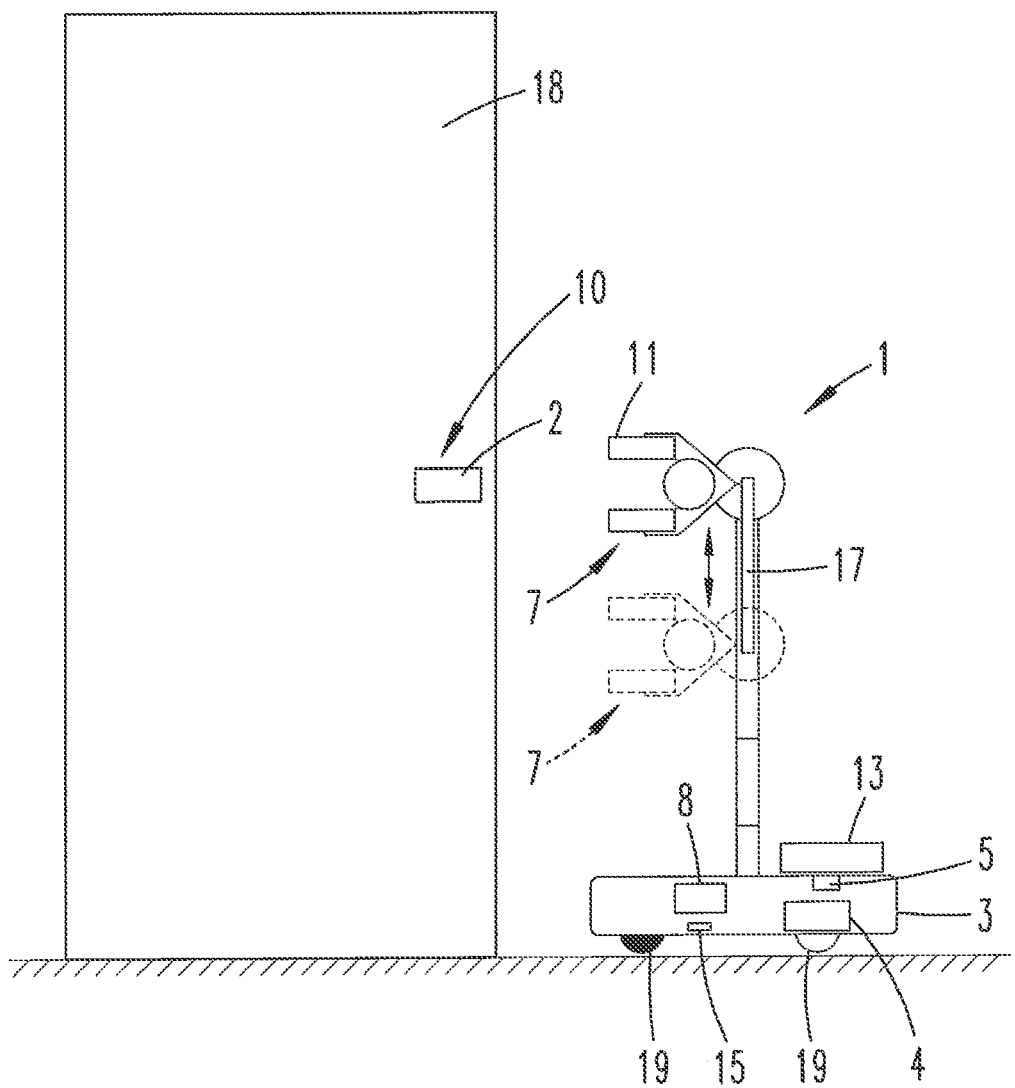

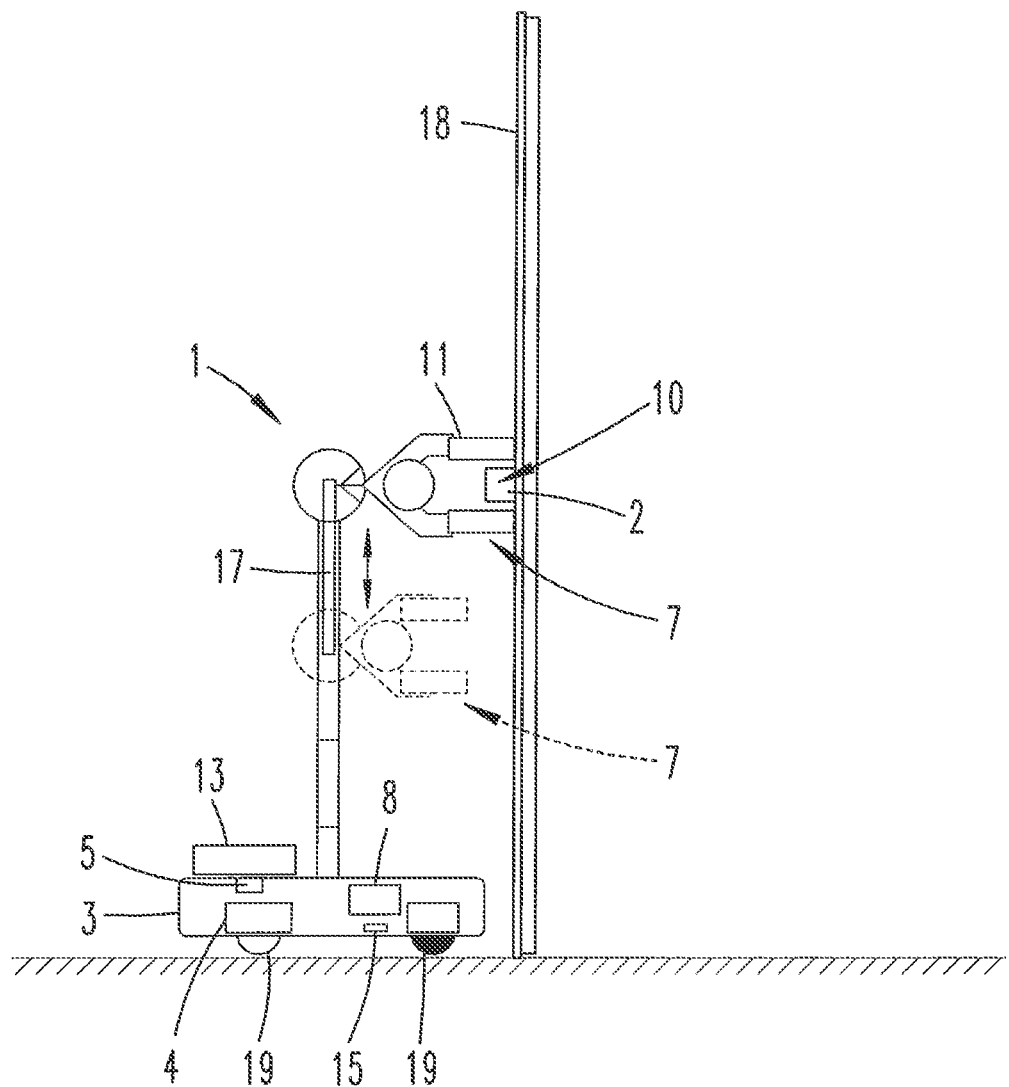

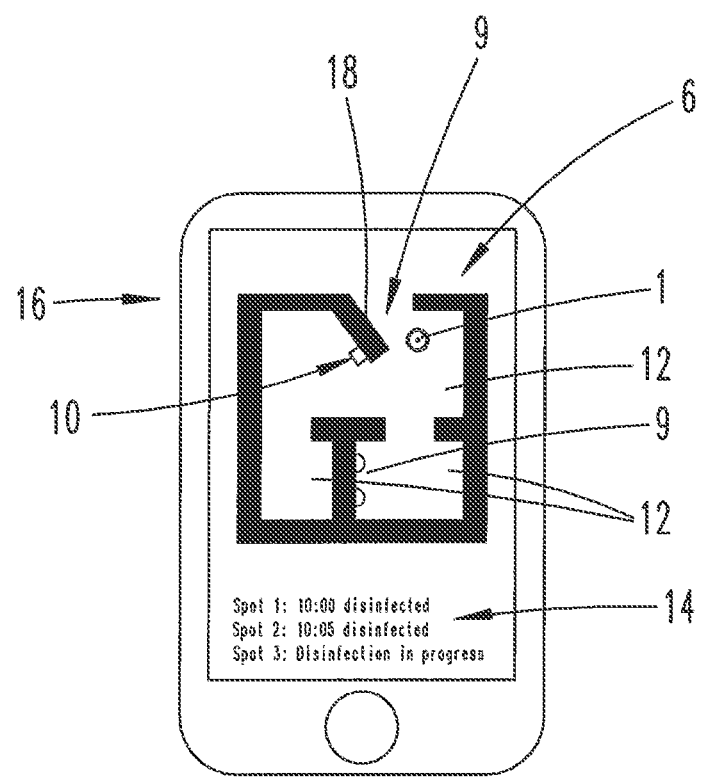

AUTOMATICALLY MOVING DISINFECTION ROBOT FOR DISINFECTING SURFACES

CROSS REFERENCE TO RELATED APPLICATIONS

Applicant claims priority under 35 U.S.C. § 119 of German Application No. 10 2020 127 988.4 filed Oct. 23, 2020, the disclosure of which is incorporated by reference.

BACKGROUND OF THE INVENTION

1. Field of the Invention

The invention relates to an automatically moving disinfection robot for disinfecting surfaces, comprising a device housing, a drive means for the movement of the disinfection robot within a surrounding area comprising at least one room, a navigation means for the navigation and self-localization of the disinfection robot within the surrounding area by means of a surrounding area map, a disinfection means for performing a disinfection activity within the surrounding area, and a control means for controlling the disinfection activity.

2. Description of the Related Art

Disinfection robots are known in the prior art, for example for the disinfection of supermarkets and warehouses, or also for the disinfection of rooms in hospitals. The disinfection robots utilize UV radiation, in particular UV-B or UV-C radiation, which is emitted into the surrounding area by luminous elements.

It is disadvantageous thereby that persons or animals must not be present in the surrounding area of the disinfection robot because the UV radiation is emitted into the surrounding area in an undirected manner and poses a risk, for example, for eyes and skin.

SUMMARY OF THE INVENTION

Based on the above-mentioned prior art, it is the object of the invention to create an automatically moving disinfection robot, which can disinfect interior spaces, in particular office spaces or sanitary spaces, without negatively impacting the health of present persons or animals.

To solve this object, an automatically moving disinfection robot is proposed, the control means of which is configured to control a locally limited disinfection in only one subregion of the room of the surrounding area, which is predefined for this purpose, or a locally limited disinfection of only one object, which is defined for this purpose, in the room of the surrounding area in a fully automated manner, wherein for attaining a locally limited disinfection effect, the disinfection means has a shielding means, namely enclosure, for separating the locally limited subregion to be disinfected from adjacent subregions of the same room, wherein the shielding means is a housing, which is open only on one side and which is placed around the object to be disinfected or against the surface to be disinfected, so that the disinfection only takes place within the housing, but not outside of the housing.

According to the invention, individual subregions or objects within a room, for example an office space, sanitary space, or space of a private household, can be systematically delimited and disinfected by means of the disinfection robot. The disinfection takes place in a fully automated manner by means of the automatically moving disinfection robot, so that no manual cleaning personnel is required in order to disinfect critical regions, such as, for example, door latches, toilets, or sinks. Due to the locally limited disinfection within the room, there is no health risk for humans or animals, which are present within the same room, but outside of the subregion of the room, which is predefined for the disinfection or locally limited object, respectively. The locations to be disinfected, namely subregions of a room or object, can be, for example, door handles, door latches, chairs, furniture handles, furniture surfaces, sanitary objects, floor subregions, or other surfaces of the surrounding area, which usually come into contact with a human or animal. For the movement in the surrounding area, the disinfection robot has a navigation means, which is suitable for the navigation and self-localization in the surrounding area. The navigation means furthermore usually has a control unit, for example a main board, optionally including a radio module for the data transmission to a drive means of the disinfection robot, which serves to drive wheels of the disinfection robot. The navigation means furthermore usually has one or several sensors for the detection of obstacles in the surrounding area. For example, the sensor can be a distance sensor, which measures distances to obstacles. A surrounding area map, which reproduces the surrounding area with rooms, subregions, and objects located therein, in particular in the form of a layout with subregions and objects recorded therein, can then be created by means of the measured distance values.

To attain a locally limited disinfection effect, the disinfection means has a shielding means, namely an enclosure, for separating the locally limited subregion to be disinfected from adjacent subregions of the same room. This shielding means is a housing, which is only open on one side and which is placed around the object to be disinfected or against the surface to be disinfected, so that the disinfection takes place only within the housing but not outside of the housing. Living beings, which are located outside of the housing, are not negatively impacted by the disinfection, in particular not damaged with respect to health. It is preferred that an open side of the shielding means, in particular of the enclosure, is placed against a surface and is thus closed, for example a floor surface or wall surface, which supports an object to be disinfected. The shielding means, in particular enclosure, can preferably be variable in size, for example by means of walls, which can be moved relative to one another, so that the size of the shielding means can be adapted to the size of an object or subregion to be disinfected. This size adaptation preferably takes place in a fully automatic manner by means of the control means of the disinfection robot. A detection means of the disinfection robot preferably recognizes a size of the object or subregion, respectively, of the room to be disinfected, and adapts the size of the shielding means accordingly.

It is furthermore proposed that the subregion of the surrounding area to be disinfected is a location point stored in the surrounding area map, a subsurface stored in the surrounding area map, or a partial volume stored in the surrounding area map. The subregion to be disinfected can thus be one-dimensional, two-dimensional, or three-dimensional. A partial volume can thereby include, for example, an object to be disinfected. A two-dimensional subregion is, for example, a surface subregion of a floor, of a wall, of a room ceiling, or the like.

It is furthermore proposed that the disinfection robot has a communication interface for predefining the subregion to be disinfected or the object to be disinfected by a user or manufacturer of the disinfection robot, and/or that the disinfection robot has a detection means for automatically recognizing the subregion to be disinfected or the object to be disinfected in the surrounding area. It can in particular also be provided that the subregion or the object, respectively, is automatically recognized by the disinfection robot and is initially reported to a user of the disinfection robot, whereupon the user can then decide whether the subregion or the object, respectively, is to be stored in the surrounding area map as having to be disinfected. It is generally proposed, however, that the locations of the surrounding area to be disinfected are either marked manually, that is, defined, by a user in the created surrounding area map, for example via an application installed on a user terminal, or are identified automatically by means of the disinfection robot, for example by means of object recognition. For the realization of an automatic recognition of an object to be disinfected, the disinfection robot can have, for example, a memory or can access an external memory, which includes information relating to defined objects, which are to be disinfected in general. Predefined objects of this type can be, for example, latches or handles on doors or pieces of furniture. By means of a feature comparison, for example as part of an image processing, a detection means of the disinfection robot can then detect whether an object or subregion within a surrounding area is an object to be disinfected or a subregion to be disinfected.

It can be provided that the control means is configured to access a disinfection plan, which is stored in a memory of the disinfection robot or an external memory, which is in data communication with the disinfection robot, wherein the disinfection plan has a specification relating to an order of several disinfection activities to be performed, a specification relating to a repetition frequency of disinfection activities, a specification relating to a disinfection performance during a disinfection activity, and/or a specification relating to a disinfection point in time of a disinfection activity. According to an embodiment, the control means of the disinfection robot can retrieve or also independently determine a sequence of the locations of the surrounding area to be disinfected from the memory. Provided that the control means is configured to independently determine the order of the disinfection at several locations, a planning specification can be, for example, a detected contamination intensity of viruses, bacteria, fungi, and the like, which are present at a location, a distance of the disinfection robot from the respective locations, an advantageous integration of the location into a planned disinfection path through the surrounding area, or the like. The control means subsequently controls the drive means of the disinfection robot to the pre-planned locations of the surrounding areas, at which a fully automatic disinfection can then take place. After the disinfection, the disinfection activity can be documented in a protocol, can in particular be stored as having been successfully concluded. For example, the successfully disinfected locations can be graphically marked in the surrounding area map, so that a user is informed particularly clearly about the disinfection process and success. To this effect, a report about the disinfection activities can be created. A stored disinfection plan can furthermore have a specification about a point in time or a repetition frequency of disinfection activities. For example, a disinfection of a certain subregion or object or also a sequence of several disinfection activities can always be started at a certain point in time, for example every evening at 8 pm or the like. In the alternative, irregularly recurring cleaning activities can also be defined. A disinfection performance can furthermore be stored, which specifies the disinfection effect. More strongly contaminated subregions or objects of the surrounding area can thus be disinfected more strongly than objects or subregions, which are only slightly contaminated in comparison.

The disinfection plan can be capable of being varied by a user of the disinfection robot, can in particular be varied with the help of an application, which is stored on an external user terminal and which is configured to access the memory. Disinfection activities can thus be specified as selected by and at the discretion of the user. The user can use a user terminal for this purpose and does not have to make the inputs himself at the disinfection robot. He can make inputs at a mobile telephone, laptop, tablet, or the like particularly comfortably in this way.

It can furthermore be provided that the disinfection means has a UV light source, in particular at least one UV LED, a plasma source, and/or a spraying means for spraying a disinfection solution. The UV light source can in particular be a light source, which emits UV light in an UV-C or UV-B spectrum, that is, in a wavelength range of from 100 nanometers to 280 nanometers (UVC) or 280 nanometers to 315 nanometers (UVB). These wavelengths are in particular suitable to remove viruses, bacteria, and fungi, or to render them harmless, respectively. Alternatively to UV light sources, a plasma source can also be used, which emits free charge carriers, in particular ions and electrons. These free charge carriers are preferably likewise suitable to render viruses, bacteria, and fungi harmless. A further embodiment can be provided that the disinfection means has a spraying means, which can spray a disinfection solution onto a subregion or an object to be disinfected. With regard to this, the spraying source is also shielded from adjacent subregions or partial volumes of the room, in particular by means of an enclosure, so that living beings, which are present in the surrounding area, do not come into contact with the disinfection solution.

Particularly preferably, the disinfection robot has a displacement means for displacing the disinfection means relative to the device housing. The displacement means can in particular be formed to cause a height change of the disinfection means. The disinfection means, preferably including the shielding means, can thus for example be adapted to various heights of a subregion or object to be disinfected. This embodiment is suitable in particular when, for example, handles, latches, or the like, which are located in an above-floor region, are to be disinfected.

The displacement means is preferably controlled by the control means, which has knowledge of the height of objects or subregions to be disinfected, respectively. The height can be determined by means of the detection means of the disinfection robot. According to an embodiment, the displacement means of the disinfection robot can also be formed to displace the disinfection means in various angular positions, so that objects or subregions to be disinfected can be disinfected from various directions.

According to a further embodiment, the disinfection robot can be a ground vehicle or an aerial drone. If it is an aerial drone, the latter can fly to the subregions or objects to be disinfected, respectively, and can disinfect them, in particular can also shield them from adjacent subregions of the room by means of the shielding means. An aerial drone is preferably also suitable to carry out a disinfection of the subregion or of the object, respectively, from the top, in particular also to spray on a spray solution from the top.

It can be provided that the disinfection robot has a detection means, which is configured to recognize living beings, in particular humans and animals, in the surrounding area, wherein the control means of the disinfection robot is configured to temporally postpone a disinfection activity, to terminate a disinfection activity, to reduce a disinfection performance, and/or to output a warning signal when the detection means detects a presence of a living being in the surrounding area. According to this design, the detection means of the disinfection robot verifies whether humans or animals are present in the surrounding area of the disinfection robot. If this is the case, the disinfection process is interrupted or is not started in the first place. The recognition of living beings can take place, for example, by means of a camera and object recognition software, by means of a LIDAR system, by means of ultrasonic sensors, by means of radar sensors, or similar detection methods. For example, a distance of a human from the disinfection robot can furthermore also be estimated, for example in that the range of a Bluetooth signal of a mobile telephone, which the user of the disinfection robot carries with him, is measured. Alternatively to an interruption or prevention of a disinfection activity of the disinfection robot, it can also be provided that a disinfection performance is reduced, namely to a level, which is non-hazardous to the health of a human or an animal. According to a further embodiment, the control means of the disinfection robot can also output an acoustic warning signal, which the user can recognize optically or in another way, that the disinfection robot currently or in the near future performs a disinfection activity in the surrounding area. Such a warning signal can in particular also be output on a user terminal, for example a mobile telephone, or the like.

As a whole, a disinfection robot is thus created by means of the invention, in the case of which a setup of the disinfection surrounding area is performed initially and subsequently a disinfection. In addition, a documentation about successfully performed or still pending disinfection activities can also be created later. For example, rooms of the surrounding area are initially recorded in a surrounding area map during the setup. Locations to be disinfected, for example subregions or objects of the room, are furthermore marked as needing to be disinfected. A definition of the manner, in which disinfection is to take place, optionally takes place, namely for example by means of disinfection solution, plasma, or UV light. A height, an angle, or another accessibility of the location can furthermore also be stored in the surrounding area map, likewise also an expected duration for the disinfection activity to be performed. The disinfection of the subregion or object, respectively, takes place subsequently, namely preferably as part of a previously specified schedule. Alternatively, the operation of the disinfection robot can also be started manually. The disinfection robot can plan a traveling distance for performing several disinfection activities in a fully automatic manner, wherein it subsequently drives or flies to a first disinfection location, aligns the disinfection means at the subregion to be disinfected or the object to be disinfected there, namely, for example, with respect to a height or an angle, and subsequently performs a disinfection. The disinfection robot subsequently moves or flies to a next defined disinfection location. The disinfection robot can subsequently create a report for a user, which includes information relating to subregions or objects of the surrounding area, which have already been disinfected or which still need to be disinfected. The user can be informed about the availability of the documentation, for example on a user terminal. The documentation can be deleted again subsequently or can be stored in a memory.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings,

FIG. 1 shows a surrounding area comprising a disinfection robot according to the invention and an object or subregion to be disinfected, respectively;

FIG. 2 shows the disinfection robot while performing a disinfection activity; and FIG. 3 shows a user terminal comprising a surrounding area map and subregions and objects to be disinfected stored therein.

DETAILED DESCRIPTION OF PREFERRED EMBODIMENTS

FIGS. 1 and 2 show a surrounding area comprising a disinfection robot 1 and an object 10 comprising a surface 2 to be disinfected. Here, the object 10 is, for example, the door handle of a door 18, which separates several rooms 12 of an apartment (see layout according to FIG. 3) from one another. Other objects 10 can also be, e.g., the door 18, pieces of furniture, decorative objects, window sills, or others.

The disinfection robot 1 has a device housing 3, a drive means 4, a navigation means 5, and a disinfection means 7. The drive means 4 serves for the movement of the disinfection robot 1 through the surrounding area and drives several wheel 19 of the disinfection robot 1. The navigation means 5 serves for the orientation and self-localization of the disinfection robot 1 in the surrounding area. A detection means 13, which is suitable for the detection of objects 10 in the surrounding area, is assigned to the navigation means 5. The detection means 13 can be, for example, a distance sensor, in particular laser sensor, which can measure distances between the disinfection robot 1 and objects 10 of the surrounding area. The detection means 13 or navigation means 5, respectively, evaluates the detected distance values and creates a surrounding area map 6 of the surrounding area, which preferably has a layout of the rooms 12 comprising objects 10 present therein. The navigation means 5 can use this surrounding area map 6 for a route planning of the disinfection robot 1 through the surrounding area. The disinfection robot 1 can in particular localize itself by means of the surrounding area map 6 and can determine its position and orientation relative to the objects 10 of the surrounding area accordingly. Subregions 9 of surrounding area, which are subsections of a room 12 of the surrounding area, for example a region below of a sink or a toilet in a bathroom, an entrance area behind a front door or the like, can also be defined in the surrounding area map 6, in addition to the objects 10.

As illustrated, the disinfection robot 1 furthermore has the disinfection means 7, which, according to different embodiments, can have a UV light source, a plasma source, and/or a spraying means for spraying a disinfection solution. A shielding means 11, which prevents that UV radiation, plasma, or disinfection solution outside of the enclosure formed by means of the shielding means 11 is released into the surrounding area, is assigned to the disinfection means 7. For this purpose, the shielding means 11 is formed in the manner of a housing, which is only open on one side (illustrated in section in FIGS. 1 and 2), namely in such a way that the shielding means 11, in cooperation with the door 18, surrounds a completely closed volume, in which the object 10 to be disinfected, namely here the door latch, is enclosed. Based on their effective length and their distance from one another, the walls of the shielding means 11 are variable relative to one another. The lengths and distances can be changed by means of a displacement means 17, which has, for example, an electric motor and guides for the displacement movements. The displacement means 17 is furthermore also configured here to perform a height change of the disinfection means 7 relative to the device housing 3 of the disinfection robot 1. With regard to the height and size of the shielded volume, the shielding means 11 as a whole can be adapted to the position and size of the object 10 or subregion 9 to be disinfected, respectively, in this way.

The disinfection robot 1 furthermore has a control means 8, which is formed to control the performance of a disinfection activity by means of the disinfection means 7. A memory 15, which includes, for example, a disinfection plan 14 with temporally defined pre-planned disinfection activities here, is assigned to the control means 8. Alternatively to a local memory 15, the memory 15 can also be a virtual memory, which is located in a so-called "cloud", that is, on a remote server, which the control means 8 of the disinfection robot 1 can access, in particular via a home communication network, in particular via WLAN, or via he Internet.

A user terminal 16 is illustrated in FIG. 3, here in the form of a mobile telephone. An application, by means of which the user can access the disinfection robot 1 in order to transmit information and control commands to the disinfection robot 1 or to obtain them from the latter, respectively, is installed on the user terminal 16. The application visualizes a layout of the surrounding area map 6, which is created by the disinfection robot 1, comprising a plurality of rooms 12 and subregions 9 as well as objects 10 defined therein, to the user of the user terminal 16. Only the latch of the door 18 is marked as object 10 in FIG. 3 only in an exemplary manner. A current position of the disinfection robot 1 is furthermore specified in the surrounding area map 6. A disinfection plan 14, which, as a whole, includes three disinfection tasks for the disinfection robot 1, namely identified with "spot 1", "spot 2", and "spot 3", is displayed below the surround area map 6. The disinfection plan 14 specifies, which subregions 9 or objects 10, respectively, of the surrounding area are to be disinfected in which chronological order. Here, the disinfection plan 14 simultaneously serves as a protocol about disinfection activities, which have already been concluded successfully. The disinfection activities "spot 1" and "spot 2" can be recognized as having been concluded already. A disinfection activity "spot 3" is still in progress.

According to a first possible embodiment, the invention works such that the user marks subregions 9 and/or objects 10, which are to be disinfected by means of the disinfection means 7 of the disinfection robot 1, in the surrounding area map 6, which is created by the disinfection robot 1. The user can thereby simultaneously also specify the order for the disinfection activities as disinfection plan 14. He can likewise provide information with respect to a type, a height, a size, and/or an orientation of the subregion 9 or object 10 to be disinfected, respectively, so that the displacement means 17 can then position and adapt the disinfection means 7 accordingly. The user subsequently starts the disinfection journey of the disinfection robot 1 via a start button (not illustrated), which is present in the application. In the alternative, it is possible that the disinfection robot 1 starts a disinfection activity in a fully automatic manner, when a predefined time for the disinfection is reached. The navigation means 5 of the disinfection robot 1 plans a path through the surrounding area, in particular the rooms 12 recorded in the surrounding area map 6, in order to reach the subregions 9 or objects 10 to be disinfected in an optimum way, which is in particular as short or energy-saving as possible. Here, the navigation means 5 initially controls, for example, the door 18 illustrated in FIG. 1 comprising the object 10 (door latch) to be disinfected, which is arranged thereon. Provided that the user has not yet left behind any information as to the height at which the object 10 is located, the detection means 13 itself can determine corresponding information relating to the object 10 to be disinfected.

The displacement means 17 then displaces the disinfection means 7 including the shielding means 11 according to FIG. 2 such that the object 10 is surrounded by the shielding means 11. The shielding means 11 is placed against the door 18 here. The door 18 and the walls of the shielding means 11 thereby form a closed housing, in which the object 10 is located. A disinfection source of the disinfection means 7 is started subsequently. The disinfection source can be, for example, a UV lamp, a plasma source, or also a spraying means for spraying a disinfection solution. While performing the disinfection, the shielding means 11 ensures that no radiation, plasma, or spray solution reaches out of the shielding means 11 into the surrounding area. As soon as the disinfection has concluded successfully, the control means 8 transmits information about the end of the disinfection activity to the memory 15, which transfers this information to the application of the user terminal 16. It is then noted in the disinfection plan 14 that the disinfection activity has ended. The disinfection plan 14 thus simultaneously serves as protocol for the disinfection activities, which have already been concluded successfully.

It can additionally be provided that the detection means 13 of the disinfection robot 1 monitors the surrounding area, and detects when a human or an animal enters the room 12, in which the disinfection robot 1 works. The detection of the human or of the animal, respectively, can take place by means of an evaluation of a camera image, or alternatively, based on the recognition of the human or animal, respectively, as quickly moving "object". Provided that the presence of a living being is recognized, the disinfection robot 1 can output, for example, a warning signal, which at least informs a human that the disinfection means 7 is currently active or will be activated shortly, respectively. In the alternative, however, the control means 8 can also terminate or postpone a disinfection activity in a fully automatic manner in this case. It can likewise also be provided that the control means 8 reduces the disinfection performance for the current disinfection activity, so that a dose, which is harmless for a human or an animal, is dispensed.

According to an alternative procedure, it can be provided that the disinfection robot 1 automatically recognizes subregions 9 to be disinfected or objects 10 to be disinfected by means of its detection means 13. This can take place, for example, by means of a sample taking and analysis of the sample with regard to viruses, bacteria, fungi, or similar substances, which are harmful to health. Provided that it is then determined that the corresponding object 10 or the corresponding subregion 9 should be disinfected, the control means 8 can transmit a disinfection command to the disinfection means 7, in order to start a disinfection activity in a fully automatic manner. In the alternative, it can also be provided that the user initially receives a message on his user terminal 16 and can then decide whether the object 10 or the subregion 9, respectively, is to actually be disinfected. The user can optionally also select the type of disinfection himself, provided that the disinfection robot 1 has various disinfection means 7, which optionally provide for a distinction by means of UV light, plasma, or distinction solution.

Even though the embodiments have been described above on the basis of a floor-supported disinfection robot 1, the disinfection robot 1 can alternatively also be an aerial drone, which can approach objects 10 or subregions 9, respectively, and which can then also perform a disinfection in particular from above. This is recommended in particular when, for example, a disinfection solution is to be sprayed onto objects 10 or subregions 9, respectively, from above.

Although only a few embodiments of the present invention have been shown and described, it is to be understood that many changes and modifications may be made thereunto without departing from the spirit and scope of the invention.

LIST OF REFERENCE NUMERALS

1 disinfection robot
2 surface
3 device housing
4 drive means
5 navigation means
6 surrounding area map
7 disinfection means
8 control means
9 subregion
10 object
11 shielding means
12 room
13 detection means
14 disinfection plan
15 memory
16 user terminal
17 displacement means
18 door
19 wheel

What is claimed is:

1. An automatically moving disinfection robot for disinfecting surfaces, comprising:
    a device housing,
    a drive means configured for the movement of the disinfection robot within a surrounding area comprising at least one room,
    a navigation means configured for navigation and self-localization of the disinfection robot within the surrounding area by means of a surrounding area map,
    a disinfection means configured for performing a disinfection activity within the surrounding area, and
    a control means configured for controlling the disinfection activity,
    wherein the control means is configured to control a locally limited disinfection in only one predefined subregion of the room of the surrounding area, or a locally limited disinfection of only one defined object, in the room of the surrounding area in a fully automated manner,
    wherein for attaining a locally limited disinfection effect, the disinfection means has a shielding means for separating the one subregion to be disinfected from adjacent subregions of the same room, wherein the shielding means is a housing, which is open only on one side and which is placed around the object to be disinfected or against the surface to be disinfected, so that the disinfection only takes place within the housing, but not outside of the housing,
    wherein the control means is configured to access a disinfection plan, which is stored in a memory of the disinfection robot or an external memory, which is in data communication with the disinfection robot,
    wherein the disinfection plan has a specification relating to an order of several disinfection activities to be performed,
    wherein a disinfection performance is stored which specifies the disinfection effect such that more strongly contaminated subregions or objects of the surrounding area are disinfected more strongly than objects or subregions which are less contaminated in comparison, and
    further comprising detection means that are configured to recognize living beings in the surrounding area, wherein the control means of the disinfection robot is configured to temporally postpone a disinfection activity, to terminate a disinfection activity, to reduce a disinfection performance, and/or to output a warning signal when the detection means detects a presence of a living being in the surrounding area.

2. The disinfection robot according to claim 1, wherein the subregion of the surrounding area to be disinfected is a location point stored in the surrounding area map, a subsurface stored in the surrounding area map, or a partial volume stored in the surrounding area map.

3. The disinfection robot according to claim 1, further comprising a communication interface for predefining the subregion to be disinfected or the object to be disinfected by a user or manufacturer of the disinfection robot, and/or further comprising a detection means for automatically recognizing the subregion to be disinfected or the object to be disinfected in the surrounding area.

4. The disinfection robot according to claim 1, wherein the disinfection plan is configured to be varied by a user of the disinfection robot, with the help of an application, which is stored on an external user terminal and which is configured to access the memory.

5. The disinfection robot according to claim 1, wherein the disinfection means has a UV light source, a plasma source, and/or a spraying means for spraying a disinfection solution.

6. The disinfection robot according to claim 1, further comprising a displacement means configured for displacing the disinfection means relative to the device housing.

7. The disinfection robot according to claim 1, wherein the disinfection robot is an aerial drone or a ground vehicle.

* * * * *